United States Patent
Rogers et al.

(10) Patent No.: US 9,999,471 B2
(45) Date of Patent: Jun. 19, 2018

(54) MALE MEDICAL IMPLEMENT CLEANING DEVICE

(71) Applicant: 3M INNOVATIVE PROPERTIES COMPANY, Saint Paul, MN (US)

(72) Inventors: Bobby E. Rogers, San Diego, CA (US); Gino Kang, Irvine, CA (US); John Detloff, San Diego, CA (US); Liam Igoe, San Diego, CA (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 610 days.

(21) Appl. No.: 13/910,053

(22) Filed: Jun. 4, 2013

(65) Prior Publication Data

US 2014/0150832 A1    Jun. 5, 2014

Related U.S. Application Data

(60) Provisional application No. 61/655,448, filed on Jun. 4, 2012.

(51) Int. Cl.
*A61L 2/18* (2006.01)
*A61B 19/00* (2006.01)
(Continued)

(52) U.S. Cl.
CPC .............. *A61B 19/34* (2013.01); *A61B 90/70* (2016.02); *A61M 39/16* (2013.01);
(Continued)

(58) Field of Classification Search
CPC .................. A61M 39/26; A61M 39/16; A61M 2039/267; A61M 39/162; A61M 39/20;
(Continued)

(56) References Cited

U.S. PATENT DOCUMENTS

| 1,744,026 A | 1/1930 | Baltzley |
| 1,841,597 A | 1/1932 | Hammer et al. |

(Continued)

FOREIGN PATENT DOCUMENTS

| DE | 2164821 A1 | 8/1972 |
| EP | 0462355 A1 | 12/1991 |

(Continued)

OTHER PUBLICATIONS

International Search Report and Written Opinion issued in International Application No. PCT/US2014/026716, dated Jun. 12, 2014.

(Continued)

*Primary Examiner* — Joseph L. Perrin
*Assistant Examiner* — Irina Graf
(74) *Attorney, Agent, or Firm* — 3M Innovative Properties Company; Lynn R. Hunsberger

(57) ABSTRACT

A cleaning device for a medical implement having a male protrusion. The cleaning device including a housing defining an inner cavity by and having an inner wall that encloses the inner cavity and an opening. The inner wall has a recess near the opening to the housing. The recess has a diameter that is greater than a diameter of the opening. The cap further includes a movable piston having a forward end and rearward end surrounded by a flexible flange that extends outward to abut the inner wall near the recess of the housing. The rearward end of the movable piston configured to contact couple with a distal end of the male protrusion to move the piston toward a distal end of the housing opposite the opening of the housing to provide a portion of the cleaning solution to the male protrusion.

11 Claims, 17 Drawing Sheets

(51) Int. Cl.
*A61M 39/16* (2006.01)
*A61M 39/20* (2006.01)
*A61B 90/70* (2016.01)

(52) U.S. Cl.
CPC ........ *A61M 39/162* (2013.01); *A61M 39/165* (2013.01); *A61M 39/20* (2013.01)

(58) Field of Classification Search
CPC ........ A61M 39/165; A61M 2039/1077; A61M 25/0097; A61M 2039/1072; A61M 39/045; A61M 5/14566; A61M 5/31511; A61M 39/14; A61M 39/18; A61M 5/001; A61M 5/1456; A61B 19/34; A61B 90/70; A61L 2202/24; B08B 9/021; B08B 9/023
See application file for complete search history.

(56) References Cited

U.S. PATENT DOCUMENTS

| | | | |
|---|---|---|---|
| 1,937,492 | A | 11/1933 | Merolle |
| 2,322,701 | A | 6/1943 | Nesset et al. |
| 2,341,285 | A | 2/1944 | Petrullo |
| 2,731,963 | A | 1/1956 | Blank |
| 2,740,480 | A | 4/1956 | Cox et al. |
| 2,993,612 | A | 7/1961 | Trautvetter |
| 3,120,879 | A | 2/1964 | Warner |
| 3,199,748 | A | 8/1965 | Bross |
| 3,362,587 | A | 1/1968 | Postel et al. |
| 3,391,847 | A | 7/1968 | Christine et al. |
| 3,405,831 | A | 10/1968 | Hudson et al. |
| 3,431,548 | A | 3/1969 | Busier et al. |
| 3,435,978 | A | 4/1969 | Wittwer |
| 3,443,686 | A | 5/1969 | Raymond et al. |
| 3,651,972 | A | 3/1972 | Itoh |
| 3,771,685 | A | 11/1973 | Micallef |
| 3,818,627 | A | 6/1974 | Lebensfeld |
| 3,979,001 | A | 9/1976 | Bogert |
| 3,987,921 | A | 10/1976 | Aichinger |
| 3,987,930 | A | 10/1976 | Fuson |
| 4,089,463 | A | 5/1978 | Babiol |
| 4,169,751 | A | 10/1979 | Yen |
| 4,232,677 | A | 11/1980 | Leibinsohn |
| 4,257,526 | A | 3/1981 | Weits et al. |
| 4,280,632 | A | 7/1981 | Yuhara |
| 4,289,248 | A | 9/1981 | Lynn |
| 4,335,756 | A | 6/1982 | Sharp et al. |
| 4,340,148 | A | 7/1982 | Beckham |
| 4,401,227 | A | 8/1983 | Pehr |
| 4,432,764 | A | 2/1984 | Lopez |
| 4,440,207 | A | 4/1984 | Genatempo et al. |
| 4,461,394 | A | 7/1984 | Sendel et al. |
| 4,530,726 | A | 7/1985 | Montiel |
| 4,564,116 | A | 1/1986 | Prohaska |
| 4,572,373 | A | 2/1986 | Johansson |
| 4,597,758 | A | 7/1986 | Aalto et al. |
| 4,624,664 | A | 11/1986 | Peluso et al. |
| 4,655,762 | A | 4/1987 | Rogers |
| 4,671,306 | A | 6/1987 | Spector |
| 4,674,643 | A | 6/1987 | Wilde et al. |
| 4,712,705 | A | 12/1987 | Fuehrer |
| 4,752,983 | A | 6/1988 | Grieshaber |
| 4,778,447 | A | 10/1988 | Velde et al. |
| 4,798,303 | A | 1/1989 | Arnold |
| 4,810,241 | A | 3/1989 | Rogers |
| 4,991,629 | A | 2/1991 | Ernesto et al. |
| 5,065,783 | A | 11/1991 | Ogle, II |
| 5,078,693 | A | 1/1992 | Shine |
| 5,143,104 | A | 9/1992 | Iba et al. |
| 5,169,033 | A | 12/1992 | Shay |
| 5,184,742 | A | 2/1993 | DeCaprio et al. |
| 5,242,425 | A | 9/1993 | White et al. |
| 5,263,606 | A | 11/1993 | Dutt et al. |
| 5,277,311 | A | 1/1994 | Hollister |
| 5,292,020 | A | 3/1994 | Narin |
| 5,385,372 | A | 1/1995 | Utterberg |
| 5,385,378 | A | 1/1995 | Hakamada et al. |
| 5,398,837 | A | 3/1995 | Degrassi |
| 5,409,471 | A | 4/1995 | Atkinson et al. |
| 5,445,270 | A | 8/1995 | Dratz |
| 5,535,771 | A | 7/1996 | Purdy et al. |
| 5,554,135 | A | 9/1996 | Menyhay |
| 5,624,402 | A | 4/1997 | Imbert |
| 5,694,978 | A | 12/1997 | Heilmann et al. |
| 5,702,017 | A | 12/1997 | Goncalves |
| 5,743,884 | A | 4/1998 | Hasson et al. |
| 5,743,894 | A | 4/1998 | Swisher |
| 5,792,120 | A | 8/1998 | Menyhay |
| 5,807,345 | A | 9/1998 | Grabenkort |
| 5,807,347 | A | 9/1998 | Bonaldo |
| 5,947,954 | A | 9/1999 | Bonaldo |
| 5,951,519 | A | 9/1999 | Utterberg |
| 5,954,957 | A | 9/1999 | Chin-Loy et al. |
| 5,989,227 | A | 11/1999 | Vetter et al. |
| 6,004,299 | A | 12/1999 | Arai et al. |
| 6,027,482 | A | 2/2000 | Imbert |
| 6,036,672 | A | 3/2000 | Allen et al. |
| 6,045,539 | A | 4/2000 | Menyhay |
| 6,102,223 | A | 8/2000 | Montgomery |
| 6,116,468 | A | 9/2000 | Nilson |
| 6,190,364 | B1 | 2/2001 | Imbert |
| 6,196,998 | B1 | 3/2001 | Jansen et al. |
| 6,224,577 | B1 | 5/2001 | Dedola |
| 6,227,391 | B1 | 5/2001 | King |
| 6,250,315 | B1 | 6/2001 | Ernster |
| 6,293,293 | B1 | 9/2001 | Wrigley et al. |
| 6,299,131 | B1 | 10/2001 | Ryan |
| 6,364,862 | B1 | 4/2002 | Bonilla |
| 6,394,983 | B1 | 5/2002 | Mayoral et al. |
| 6,520,935 | B1 | 2/2003 | Jansen et al. |
| 6,523,686 | B1 | 2/2003 | Bae |
| 6,524,295 | B2 | 2/2003 | Daubert et al. |
| 6,527,751 | B2 | 3/2003 | Fischer et al. |
| 6,622,882 | B2 | 9/2003 | Smith |
| 6,821,267 | B2 | 11/2004 | Veillon, Jr. et al. |
| 6,880,801 | B2 | 4/2005 | Matkovich et al. |
| 6,911,025 | B2 | 6/2005 | Miyahara |
| 6,913,157 | B2 | 7/2005 | Oh |
| 7,083,605 | B2 | 8/2006 | Miyahara |
| 7,090,191 | B2 | 8/2006 | Matkovich et al. |
| 7,118,560 | B2 | 10/2006 | Bonaldo |
| 7,188,623 | B2 | 3/2007 | Anderson et al. |
| 7,198,611 | B2 | 4/2007 | Connell et al. |
| 7,282,186 | B2 | 10/2007 | Lake, Jr. et al. |
| 7,316,669 | B2 | 1/2008 | Ranalletta |
| 7,329,235 | B2 | 2/2008 | Bertron et al. |
| 7,329,249 | B2 | 2/2008 | Bonaldo |
| 7,427,275 | B2 | 9/2008 | DeRuntz et al. |
| 7,452,349 | B2 | 11/2008 | Miyahara |
| 7,500,964 | B2 | 3/2009 | Shaw et al. |
| 7,530,977 | B2 | 5/2009 | Lodi |
| 7,682,561 | B2 | 3/2010 | Davis et al. |
| 7,704,002 | B2 | 4/2010 | Fisher et al. |
| 7,780,794 | B2 | 8/2010 | Rogers et al. |
| 7,857,793 | B2 | 12/2010 | Raulerson et al. |
| 7,922,701 | B2 | 4/2011 | Buchman |
| 7,931,618 | B2 | 4/2011 | Wyrick |
| 7,931,877 | B2 | 4/2011 | Steffens et al. |
| 7,967,779 | B2 | 6/2011 | Bertron et al. |
| 7,985,302 | B2 | 7/2011 | Rogers et al. |
| 7,988,676 | B1 | 8/2011 | Gray |
| 8,061,544 | B2 | 11/2011 | Frishman |
| 8,105,293 | B2 | 1/2012 | Pickhard |
| 8,162,899 | B2 | 4/2012 | Tennican |
| 8,167,847 | B2 | 5/2012 | Anderson et al. |
| 8,172,813 | B2 | 5/2012 | Janish |
| 8,177,768 | B2 | 5/2012 | Leinsing |
| 8,197,749 | B2 | 6/2012 | Howlett et al. |
| 8,206,514 | B2 | 6/2012 | Rogers et al. |
| 8,231,587 | B2 | 7/2012 | Solomon et al. |
| 8,277,422 | B2 | 10/2012 | Oliver et al. |
| 8,287,491 | B2 | 10/2012 | Burns et al. |
| 8,296,893 | B2 | 10/2012 | Vinci et al. |
| 8,303,548 | B2 | 11/2012 | Ito et al. |

(56) References Cited

U.S. PATENT DOCUMENTS

| | | | |
|---|---|---|---|
| 8,641,681 B2 | 2/2014 | Solomon et al. | |
| 8,647,326 B2 | 2/2014 | Solomon et al. | |
| 8,832,894 B2 | 9/2014 | Rogers et al. | |
| 8,834,650 B2 | 9/2014 | Rogers et al. | |
| 2001/0003150 A1 | 6/2001 | Imbert | |
| 2002/0133124 A1 | 9/2002 | Leinsing et al. | |
| 2004/0024357 A1 | 2/2004 | Pelkey et al. | |
| 2004/0030321 A1 | 2/2004 | Fangrow | |
| 2004/0039341 A1 | 2/2004 | Ranalletta | |
| 2004/0138626 A1* | 7/2004 | Cote, Sr. | A61M 39/26 604/249 |
| 2004/0171993 A1 | 9/2004 | Bonaldo | |
| 2004/0172006 A1 | 9/2004 | Bonaldo | |
| 2004/0195136 A1 | 10/2004 | Young et al. | |
| 2004/0258560 A1 | 12/2004 | Lake et al. | |
| 2005/0124970 A1 | 6/2005 | Kunin et al. | |
| 2005/0147524 A1 | 7/2005 | Bousquet | |
| 2005/0147525 A1 | 7/2005 | Bousquet | |
| 2005/0214185 A1 | 9/2005 | Castaneda | |
| 2006/0030827 A1 | 2/2006 | Raulerson | |
| 2006/0048313 A1 | 3/2006 | Yamaki | |
| 2006/0189961 A1 | 8/2006 | Miyahara | |
| 2006/0253103 A1 | 11/2006 | Utterberg et al. | |
| 2007/0106205 A1 | 5/2007 | Connell et al. | |
| 2007/0106229 A1 | 5/2007 | Wong | |
| 2007/0112333 A1 | 5/2007 | Hoang et al. | |
| 2007/0156118 A1 | 7/2007 | Ramsey et al. | |
| 2007/0176117 A1 | 8/2007 | Redmond et al. | |
| 2008/0019889 A1 | 1/2008 | Rogers et al. | |
| 2008/0027399 A1 | 1/2008 | Harding et al. | |
| 2008/0038167 A1 | 2/2008 | Lynn | |
| 2008/0039803 A1 | 2/2008 | Lynn | |
| 2008/0086091 A1 | 4/2008 | Anderson et al. | |
| 2008/0095680 A1 | 4/2008 | Steffens et al. | |
| 2008/0128646 A1 | 6/2008 | Clawson | |
| 2008/0132880 A1 | 6/2008 | Buchman | |
| 2008/0147047 A1 | 6/2008 | Davis et al. | |
| 2008/0177250 A1 | 7/2008 | Howlett et al. | |
| 2008/0287855 A1 | 11/2008 | Hoffmann | |
| 2009/0005759 A1 | 1/2009 | Chelak | |
| 2009/0008393 A1 | 1/2009 | Howlett et al. | |
| 2009/0028750 A1 | 1/2009 | Ryan | |
| 2009/0062766 A1 | 3/2009 | Howlett et al. | |
| 2009/0099529 A1 | 4/2009 | Anderson et al. | |
| 2009/0137969 A1 | 5/2009 | Colantonio et al. | |
| 2009/0149819 A1 | 6/2009 | Chelak | |
| 2009/0163876 A1 | 6/2009 | Chebator et al. | |
| 2009/0171322 A1 | 7/2009 | Kurimoto | |
| 2009/0205151 A1 | 8/2009 | Fisher et al. | |
| 2010/0000040 A1 | 1/2010 | Shaw et al. | |
| 2010/0047123 A1 | 2/2010 | Solomon et al. | |
| 2010/0049170 A1 | 2/2010 | Solomon et al. | |
| 2010/0050351 A1 | 3/2010 | Colantonio et al. | |
| 2010/0172794 A1 | 7/2010 | Ferlic et al. | |
| 2010/0174162 A1 | 7/2010 | Gough et al. | |
| 2010/0199448 A1 | 8/2010 | Vazales et al. | |
| 2010/0312197 A1 | 12/2010 | Sano et al. | |
| 2010/0313366 A1 | 12/2010 | Rogers et al. | |
| 2011/0066119 A1* | 3/2011 | Cote, Sr. | A61M 39/045 604/288.03 |
| 2011/0165020 A1 | 7/2011 | Tryggvason | |
| 2011/0213341 A1 | 9/2011 | Solomon et al. | |
| 2011/0265825 A1 | 11/2011 | Rogers et al. | |
| 2011/0277788 A1 | 11/2011 | Rogers et al. | |
| 2012/0039764 A1 | 2/2012 | Solomon et al. | |
| 2013/0019421 A1 | 1/2013 | Rogers et al. | |
| 2013/0237911 A1 | 9/2013 | Von Schuckmann | |
| 2014/0101876 A1 | 4/2014 | Rogers et al. | |
| 2014/0228773 A1 | 8/2014 | Burkholz | |

FOREIGN PATENT DOCUMENTS

| | | |
|---|---|---|
| EP | 1061000 A2 | 12/2000 |
| EP | 1977714 A1 | 10/2008 |
| EP | 2135626 A1 | 12/2009 |
| JP | 07-047137 | 2/1995 |
| JP | 07-043674 | 9/1995 |
| JP | 09-206370 A | 8/1997 |
| JP | 09-012829 U | 9/1997 |
| JP | 2001-527441 A | 12/2001 |
| JP | 2002-291906 A | 10/2002 |
| JP | 2006-166961 | 6/2006 |
| JP | 2007-244706 | 9/2007 |
| JP | 2007-296317 | 11/2007 |
| JP | 2008-506465 | 3/2008 |
| JP | 4234777 B1 | 3/2009 |
| JP | 2009-526617 | 7/2009 |
| JP | 2009-543662 | 12/2009 |
| WO | WO-94/11474 A1 | 5/1994 |
| WO | WO-98/48872 A1 | 11/1998 |
| WO | WO-00/24442 A1 | 5/2000 |
| WO | WO 2007/054233 | 3/2007 |
| WO | WO-2007/103998 A2 | 9/2007 |
| WO | WO 2007/112944 | 10/2007 |
| WO | WO-2007137056 A2 | 11/2007 |
| WO | WO-2009136957 A1 | 11/2009 |
| WO | WO-2009/153224 A1 | 12/2009 |
| WO | WO 2011/028722 | 3/2011 |
| WO | WO-2011056221 A1 | 5/2011 |
| WO | WO-2011120017 A1 | 9/2011 |

OTHER PUBLICATIONS

U.S. Appl. No. 60/815,806, filed Jun. 22, 2006, Anderson et al.

U.S. Appl. No. 60/832,437, filed Jul. 21, 2006, Rogers.

Byington "Spontaneously Generating Life in Your Classroom? Pasteur, Spallanzani & Science Process," *The American Biology Teacher*, vol. 63, No. 5 (May 2001). pp. 340-345. Published by University of California Press on behalf of National Association of Biology Teachers.

European Patent Office, European Search Report and Opinion for EP Application No. EP 10 78 3956, date of completion of the search Mar. 12, 2014, 7 pgs.

European Patent Office, Supplementary Partial European Search Report and Opinion for EP Application No. 07 75 8117 date of completion of the search Nov. 22, 2012, 6 pgs.

International Search Report and Written Opinion issued in International Application No. PCT/US2008/053744, dated Jul. 22, 2009.

International Search Report and Written Opinion issued in International Application No. PCT/US2012/025517, dated Nov. 9, 2012.

International Standard ISO 594-2. "Conical Fitting with 6% (Luer) Taper for Syringes, Needles and Certain Other Medical Equipment—Part 2: Lock Fittings". Reference No. ISO 594-2:1998(E). Second edition. (Sep. 1, 1998)1:11.

Japanese Patent Office, Japanese Notice of Reasons for Rejection for Japanese Patent Application No. 2008-558527 dated Apr. 12, 2012.

Japanese Patent Office, Japanese Notice of Reasons for Rejection for Japanese Patent Application No. 2008-558527 dated Apr. 2, 2013.

Material Properties of Polyamide (Nylon), www.madeitfrom.com, pp. 1-2. Retrieved Sep. 23, 2012.

Material Properties of Polycarbonate, www.madeitfrom.com, pp. 1-3. Retrieved Sep. 23, 2012.

Material Properties of Polypropylene, www.madeitfrom.com, pp. 1-2. Retrieved Sep. 23, 2012.

Menyhay et al. "Disinfection of Needleless Catheter Connectors and Access Ports with Alcohol May Not Prevent Microbial Entry: The Promise of a Novel Antiseptic-Barrier Cap". *The University of Chicago Press on behalf of The Society for Healthcare Epidemiology of America. Infect Control Hosp Epidemiol.* vol. 27(2006):23-27.

Menyhay Healthcare Systems LLC available at http://www.menyhaymedical.comimenyhay.html (retrieved Nov. 8, 2013).

The International Bureau of WIPO, PCT International Preliminary Report on Patentability and Written Opinion of the International Searching Authority for International Application No. PCT/US2007/063534 dated Nov. 21, 2007.

(56) References Cited

OTHER PUBLICATIONS

Value Plastics Inc, Luer Connectors, http://www.valueplasctics.com/search/search.aspx, pp. 1-2. Retrieved Sep. 23, 2012.
PCT Search Report and Written Opinion dated Oct. 16, 2013 for PCT application No. PCT/US2013/044167.

* cited by examiner

MALE MEDICAL IMPLEMENT CLEANING DEVICE

CROSS REFERENCE TO RELATED APPLICATION

This application claims priority under 35 U.S.C. § 119(e) to U.S. Provisional Patent Application Ser. No. 61/655,448, filed Jun. 4, 2012 and entitled "Male Medical Implement Cleaning Device", the disclosure of which identified in this paragraph is incorporated by reference herein in its entirety.

BACKGROUND

The present application relates to cleaning devices for a medical implement, and more particularly to a cleaning cap for a male luer A luer is a standardized system of fluid fittings, ports and interfaces used for making fluid-tight connections between medical implements. For instance, some male luers include a tapered male protrusion defining a lumen, where the protrusion extends out from a sleeve or chamber that has internal threads on an inner wall of the chamber. A luer lock or other female port with or without an external thread can be fitted into the sleeve and over the male protrusion, for a friction-based fitting on the male protrusion. A male luer can be used on syringes, injection ports, or other intravenous (IV) lines.

One conventional solution for protection of a male luer is known as a "dual cap". This device has a cap used to disinfect luer access valves and has a second cap used to cap the male distal end of an IV. However, there is no one-to-one ratio of these two caps for a single access line female-to-male luer interface. Thus, many caps of this set of two caps will be wasted. Further, there is the issue of throwing away unused caps and their associated costs and inconvenience. Also, this system has too many parts, also adding to cost to manufacture.

SUMMARY

This document describes a cleaning cap for a male medical implement having a male protrusion. The cleaning cap includes a housing defining an inner cavity. The housing has an inner wall and distal end that encloses the inner cavity, and an opening opposite the distal end. The inner wall has a recess near the opening to the housing. The opening has a diameter that is less than a diameter of the recess, and the diameter of the opening includes one or more vents from the inner cavity. The cleaning cap further includes a cleaning solution in the inner cavity of the housing, and a movable piston to maintain the cleaning solution in the inner cavity prior to receipt of the male protrusion. The piston has a forward nose and rearward end surrounded by a flexible flange that extends outward and toward the opening to abut the inner wall near the recess of the housing into the inner cavity, the rearward end of the movable piston configured to couple with a distal end of the male protrusion to move the piston toward the distal end of the housing opposite the opening of the housing to provide a portion of the cleaning solution to the male protrusion.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

FIGS. 13A-13B are an perspective alternative view and a cross-sectional alternative view of the cap and the piston.

Like reference symbols in the various drawings indicate like elements.

DETAILED DESCRIPTION

This document describes a cleaning device for a medical implement, particularly a male medical implement such as a male luer that includes a male protrusion protruding from an inner cavity of a sleeve and extending beyond an opening to the sleeve. In some implementations, the cleaning device is a cap with a sliding piston within the cap that maintains a cleaning solution within an inner cavity of the cap, until the sliding piston is pushed further toward the inner cavity by the male protrusion of the male luer to cause cleaning solution to flow around the sliding piston and bathe some or all of the male protrusion and some or all of the sleeve around the male protrusion. The cap can include a removable seal to maintain the cleaning solution and the piston in the inner cavity until the cap is placed over the male protrusion and/or into the sleeve. The removable seal can be a foil-based seal, in the shape of a pull-tab, and can be heat-welded or thermally bonded, glued or otherwise attached at an opening to the inner cavity. In some other implementations, the cap can include a plug or other sealing member for sealing the opening to the inner cavity.

Figure 1:
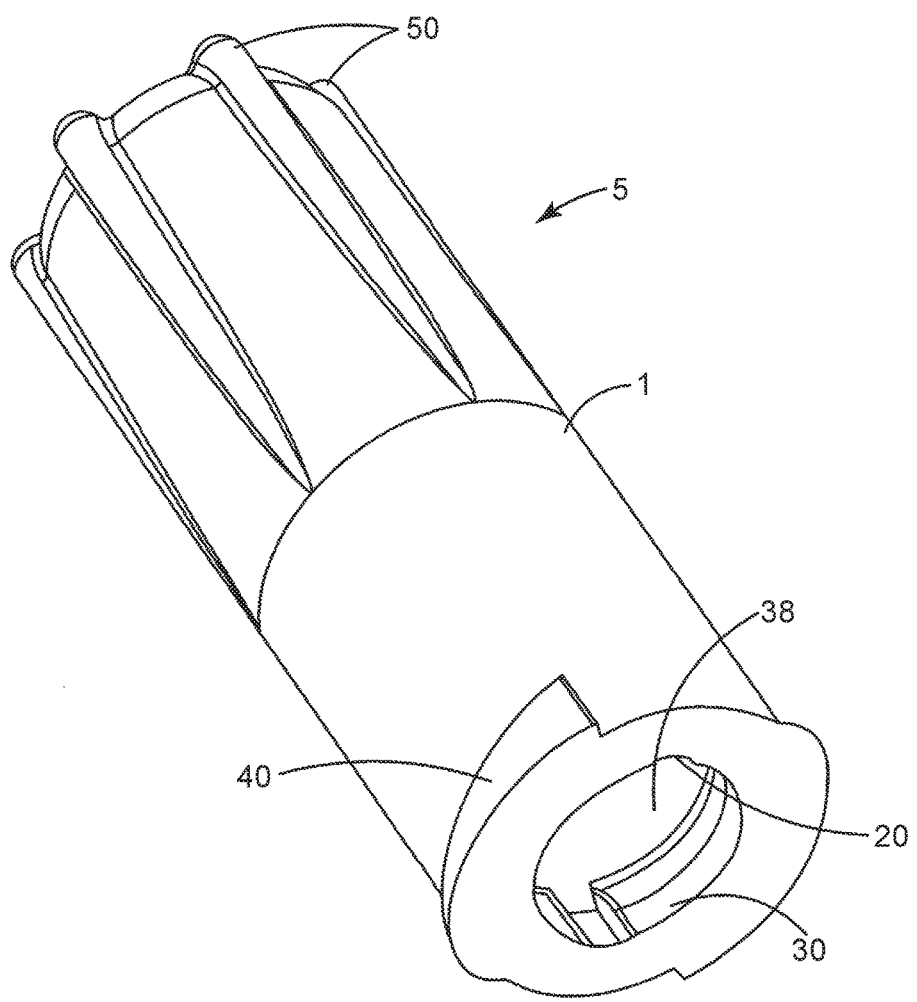
FIG. 1 is a perspective view of a cap.

FIG. 1 is a perspective view of a cap 5 in accordance with an exemplary implementation. The cap includes a housing 1 that defines an inner cavity 38 that is closed on all sides except at an opening 30. The housing 1 is preferably cylindrical, and the inner cavity 38 is likewise preferably cylindrical with a closed distal end that is opposite the opening 30. An outer surface of the housing 1 can have one or more ribs 50 or ridges, flanges, tabs, etc., for allowing gripping by a user's fingers, for example. An inner periphery of the inner cavity 38 at the opening 30 can include one or more vents 20. In some implementations, the vents 20 can be cut-outs, notches or insets at the opening 30, or areas that have an increased diameter than the rest of the opening 30. In other implementations, the vents 20 can be holes or apertures that are proximate to but separate from the opening 30. The housing 1 further includes one or more threads, protrusions, flanges, or the like, extending out externally from an outer periphery of the housing 1 near the opening 30, to engage with the threads of a male luer sleeve. In preferred implementations, the one or more threads 40 include two at least partial threads extending from opposite sides of the housing 1 at the opening 30.

Figure 2:
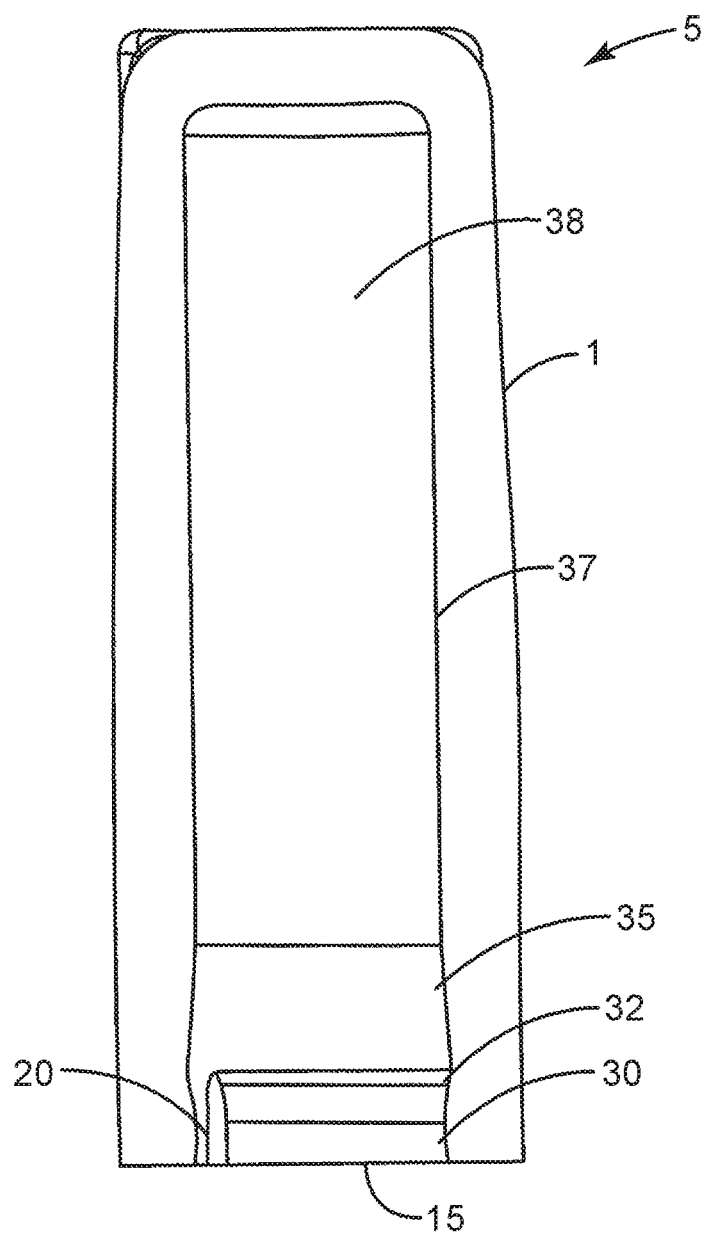
FIG. 2 is a side cross-sectional view of the cap.

FIG. 2 is a side cross-sectional view of a cap 5 in accordance with the exemplary implementation, and showing an inner cavity 38 defined by the housing 1 and an inner wall 37 of the housing 1. The inner wall 37 is preferably cylindrical of a substantially uniform diameter, however toward the opening and proximal end 15 the diameter of the inner wall 37 widens by wider diameter regions 35 to one or more recesses 32, i.e., a maximum diameter of the inner cavity, before the diameter narrows again at the diameter of the opening 30, exclusive of the one or more vents 20. The one or more recesses 32 can also include a recessed inner wall (i.e. large diameter) around the circumference of the inner wall 37 at the recess 32. Alternatively, the one or more recesses 32 can occupy less than the full circumference of the inner wall 37.

Figure 3:
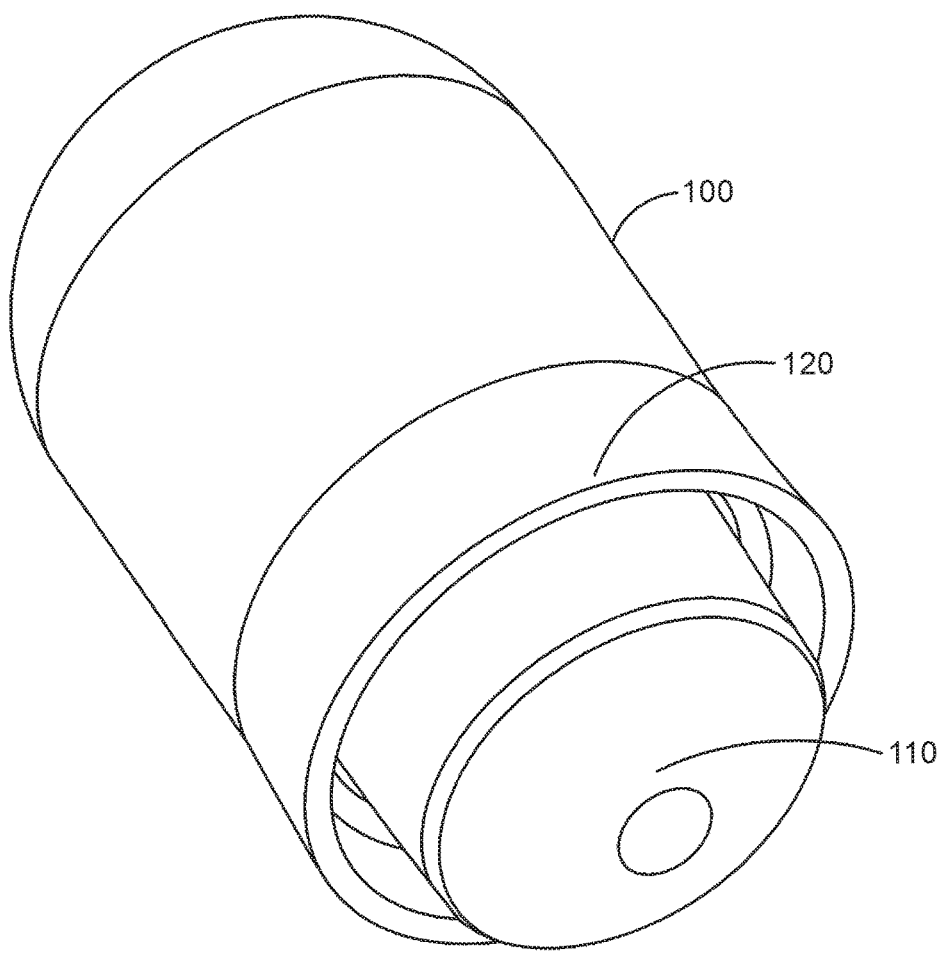
FIG. 3 is a perspective view of a pill that is configured to reside in the cap.
Figure 4:
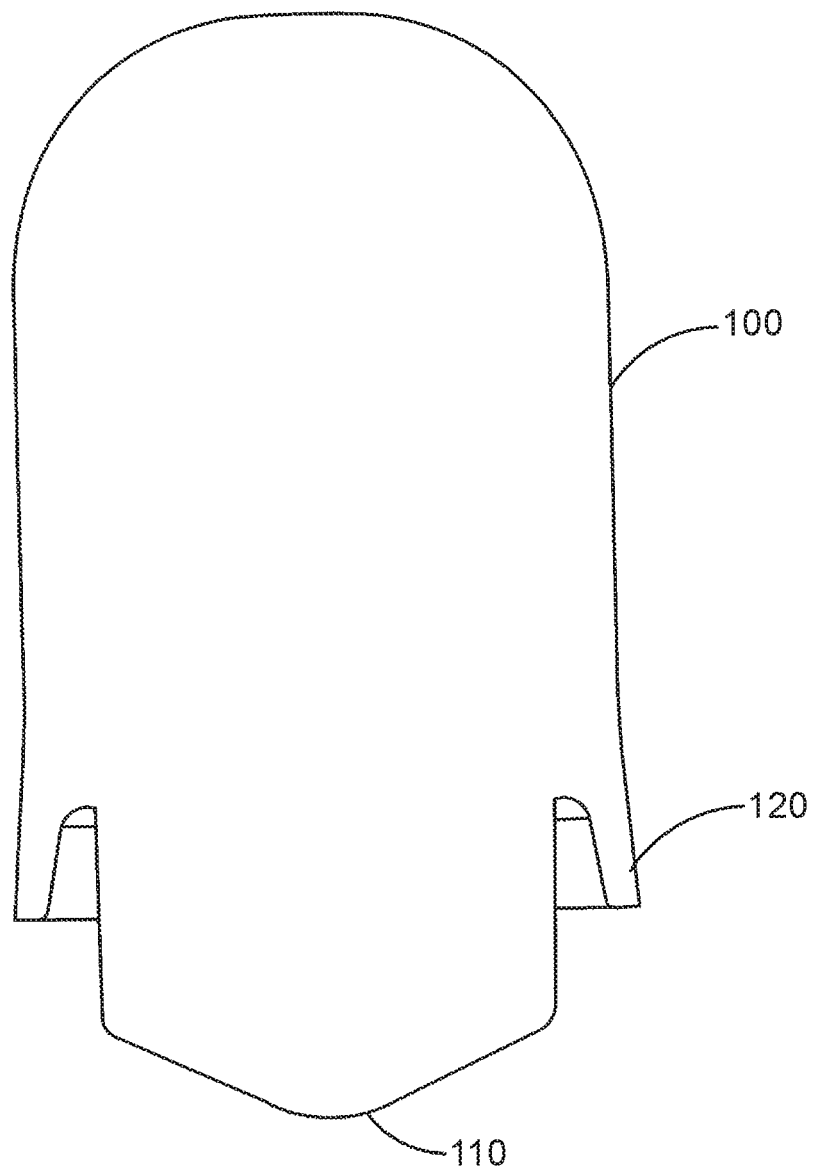
FIG. 4 is a side cross-sectional view of one implementation of the pill.

FIG. 3 is a perspective view of a slidable piston 100 (or "pill") that is configured to reside in the cap and retain a cleaning solution or cleaning fluid within the inner cavity of the housing until pushed by a male protrusion of a male luer. FIG. 4 is a side cross-sectional view of one implementation of the piston 100. The piston 100 is rounded or generally cylindrical in shape, with a rounded or smooth nose or forward end that is configured for being directed toward a distal end of the inner cavity of the housing. The piston 100 also includes a male protrusion interface surface 110, or rearward end, which can also be rounded or smooth, or which preferably can include one or more grooves, channels, or raised portions. The piston 100 further includes a sealing skirt 120 of flexible material. The sealing skirt 120 is flexible and is sized to be slightly wider than the recess 32 and the inner wall 37 of the inner cavity of the housing 1, to be biased against or provide force against the recess 32 and the inner wall 37 to inhibit movement of the piston 100. Additionally, the skirt 120 flares away from the piston 100 and downward and opposite from the nose of the piston 100 at an angle substantially to correspond with a tapering of the wider diameter or tapered diameter region 35, and to circumscribe some or all of the male protrusion interface surface 110.

Figure 5:
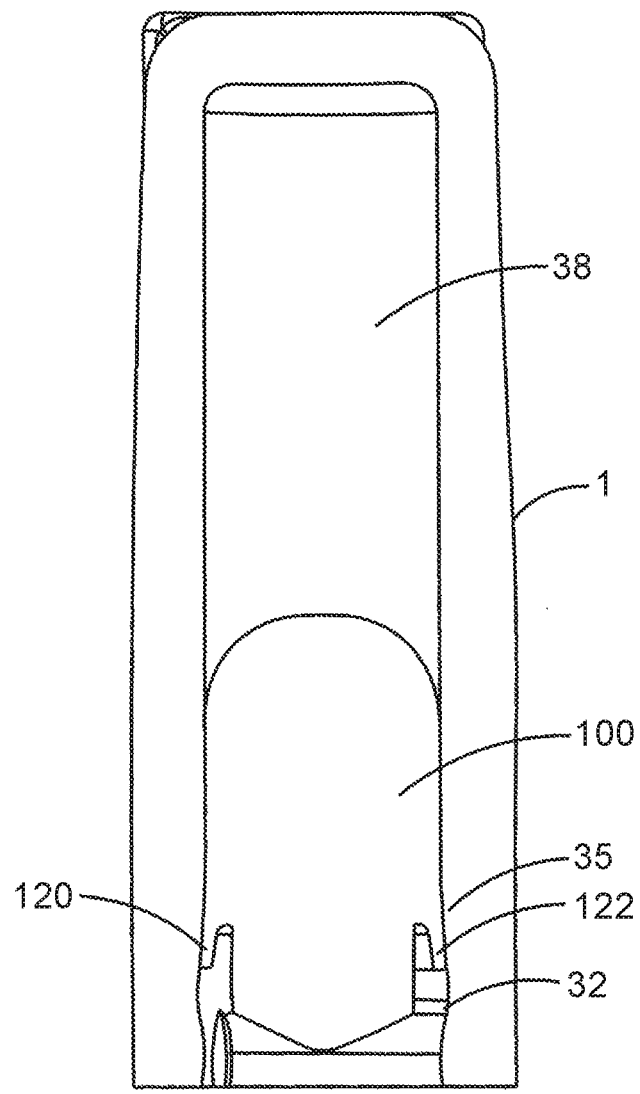
FIG. 5 illustrates the pill inside the cap prior to insertion of a male medical implement.

FIG. 5 illustrates the piston 100 inside the housing 1 of the cap prior to insertion of a male protrusion of a medical implement such as a male luer. As can be seen, the ends 122 of the skirt 120 of the piston extend against the tapered region 35 of the inner wall of the housing toward the recess 32 of the inner wall. Some or all of the portion of the inner cavity 38 opposite the piston 100 from the opening can be filled with a cleaning solution or liquid or cleaning fluid.

Figure 6:
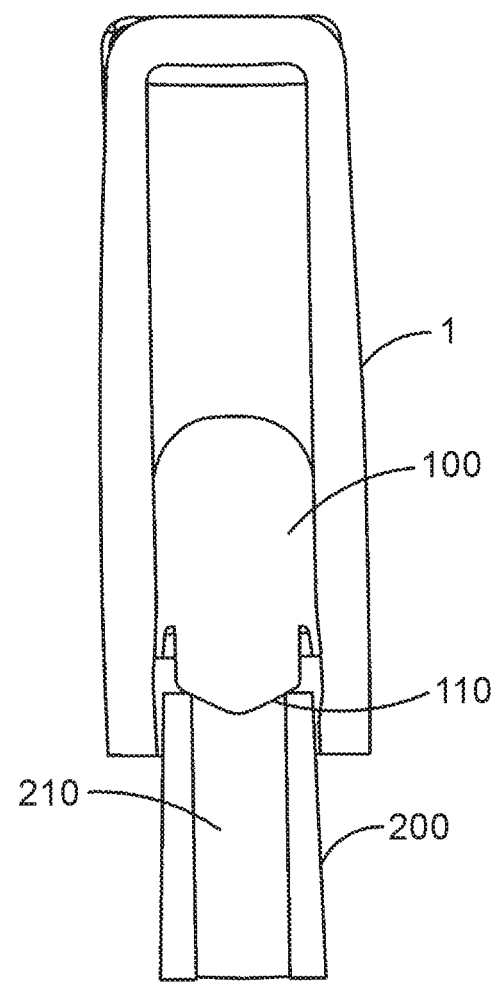
FIG. 6 illustrates the beginning of insertion of the male medical implement.

FIG. 6 illustrates the beginning of insertion of a male protrusion 200 of a medical implement, in which a distal end of the male protrusion 200 contacts the piston 100 via the male protrusion interface surface 110, which may or may not seal the lumen 210 of the male protrusion 200. In some implementations, any gap in between the distal end of the male protrusion and the male protrusion interface surface 110 of the piston is smaller or of less area than the vents in the housing, such that the cleaning solution or cleaning fluid will take the path to least resistance and prefer to exit, under pressure from the piston, through the vents as opposed to entering the lumen 210.

Figure 7:
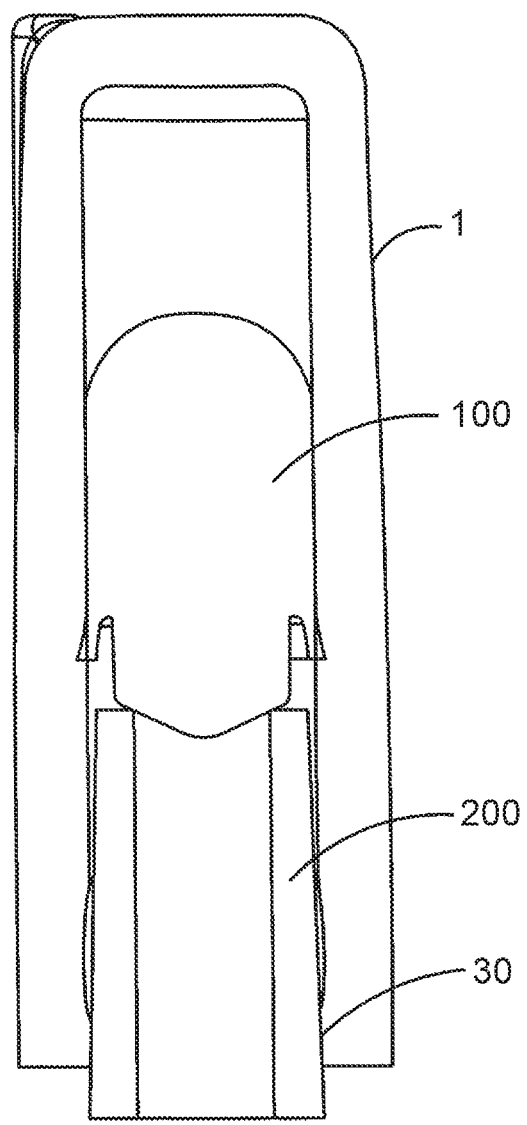
FIG. 7 illustrates further insertion of the male medical implement.

FIG. 7 illustrates further insertion of the male protrusion 200 into the inner cavity 38 of the housing 1, pushing the piston 100 further toward the distal end of the inner wall of the housing, and to further pressure cleaning solution or cleaning fluid around the piston to bathe at least a portion of the male protrusion 200 with the cleaning solution or fluid to disinfect or clean that portion, which cleaning can also address the tip and/or distal end of the lumen. As described above, the male protrusion 200 is tapered (approximately 6 degrees, by industry standard), and will eventually wedge into the inner diameter of the opening 30, to form a friction-based fitting of the cap onto the male protrusion 200. A reverse direction between the male protrusion 200 and the cap (i.e. pulling the cap off the male medical implement, or pulling the male medical implement from the cap, or a combination of the two), after overcoming the friction-based fitting, will disengage the cap from the male protrusion 200.

Figure 8:
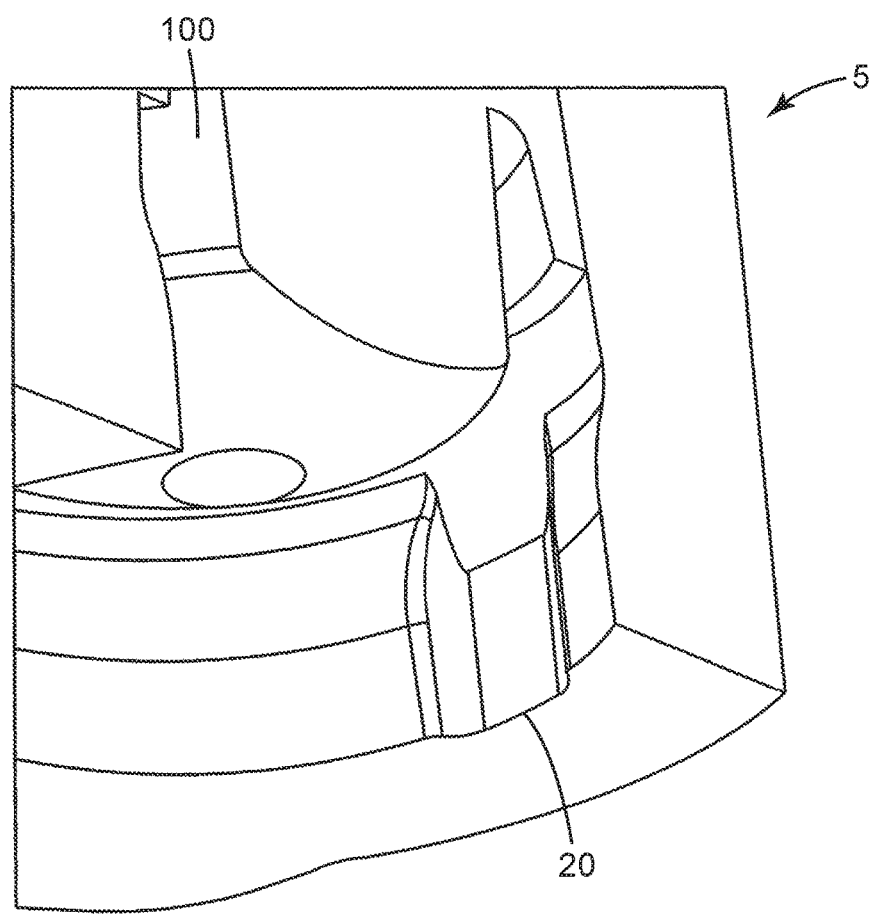
FIG. 8 is a perspective view of a section of the cap and the pill, and shows a vent at an opening to the cap.
Figure 9:
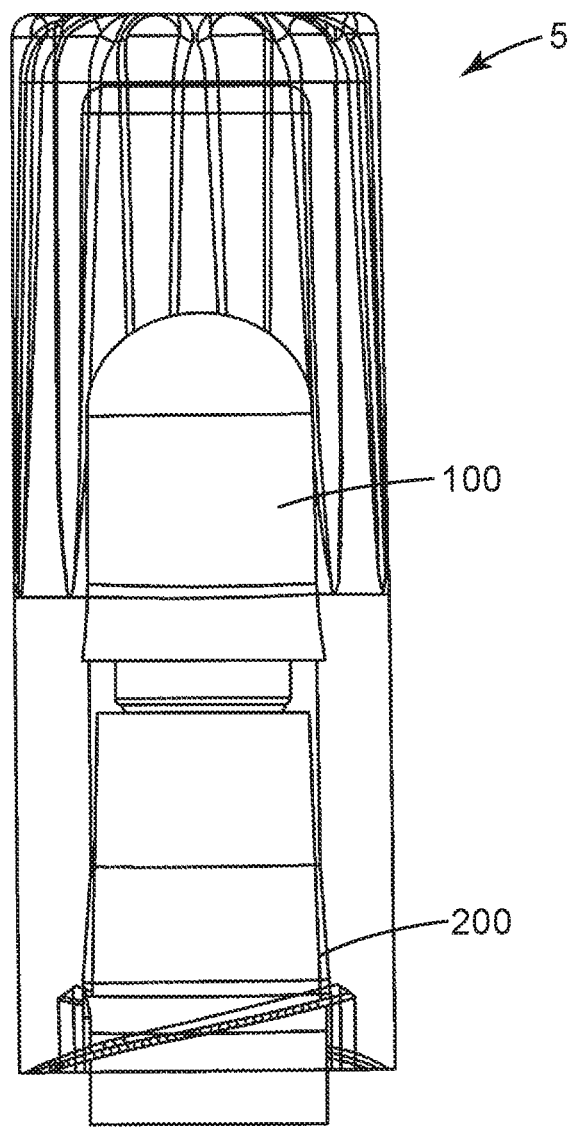
FIG. 9 is a transparent view of a cap and pill with an inserted male medical implement.
Figure 10:
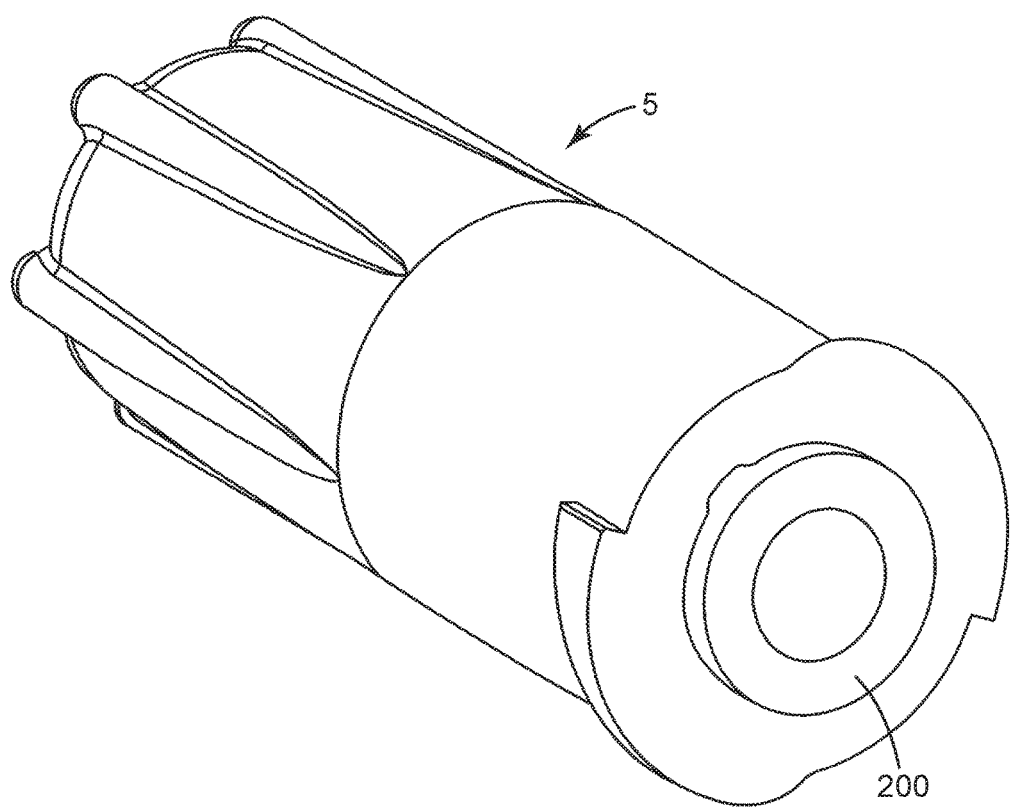
FIG. 10 is a perspective or isometric view of the device.
Figure 11:
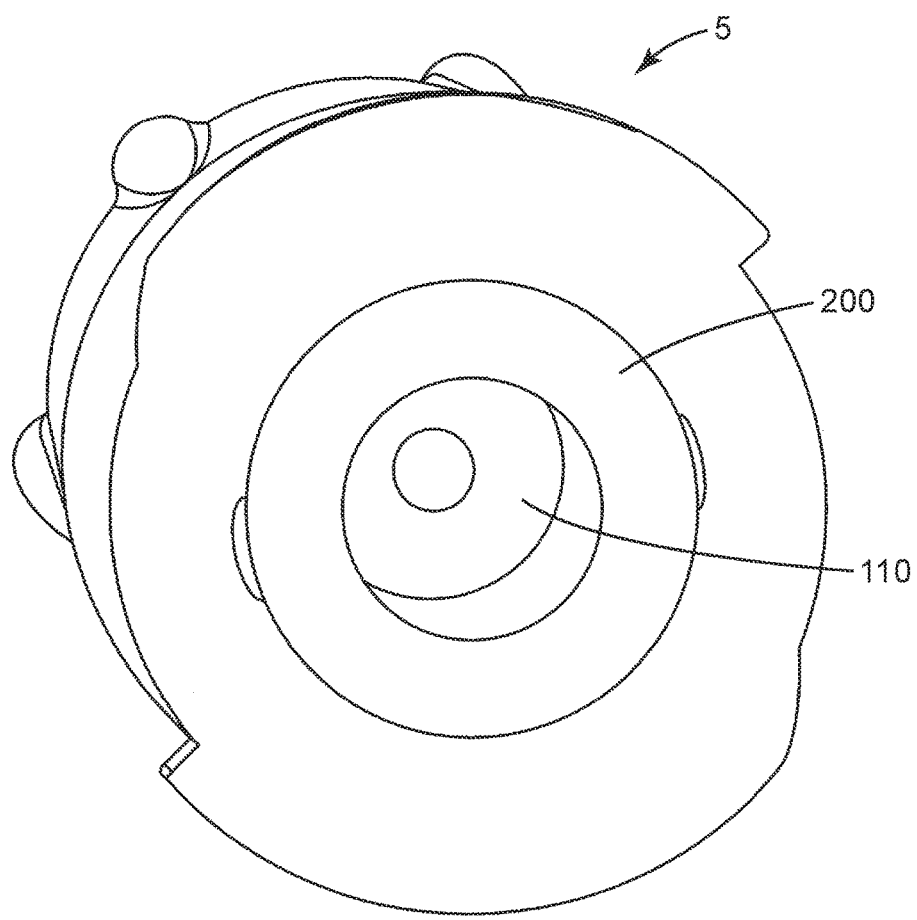
FIG. 11 is an end view of the device with the inserted male medical implement.
Figure 12A:
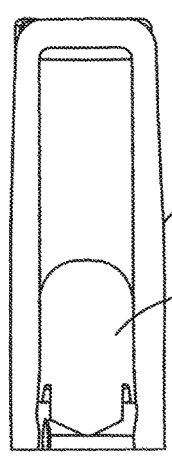
FIGS. 12A-12C show a sequence of stages of cleaning a male medical implement.
Figure 12B:
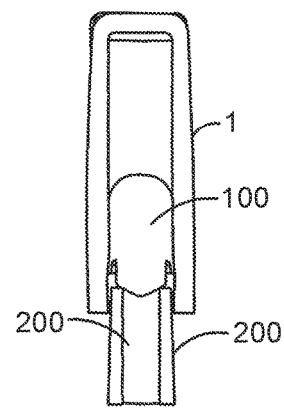
Figure 12C:
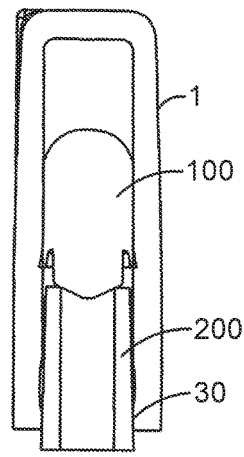
Figure 13B:
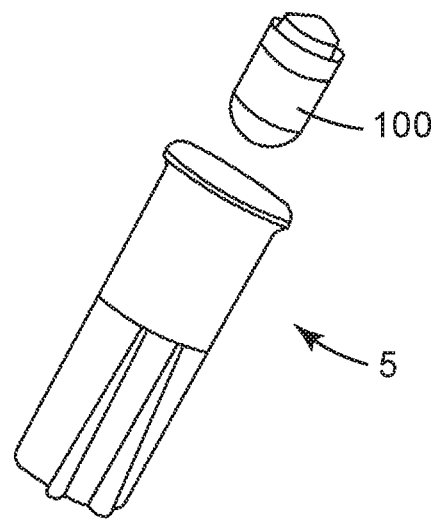
Figure 13B:
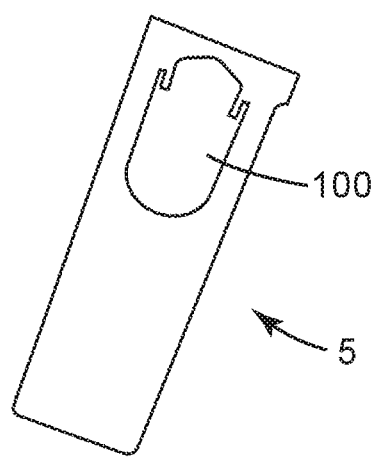

FIG. 8 is a perspective view of a section of the cap 5 and the piston 100, prior to insertion by a male protrusion, and shows a vent 20 at an opening to the cap. FIG. 9 is a transparent view of a cap 5 and piston 100 with an inserted male medical implement, while FIG. 10 is a perspective or isometric view of the cap 5 with an inserted male protrusion 200. FIG. 11 is an end view of the cap 5 toward the opening, with the inserted male protrusion 200 and a view of the male protrusion interface surface 110 of the piston seen through the lumen of the male protrusion 200. FIGS. 12A-12C illustrate again a sequence of stages of cleaning a male medical implement. FIGS. 13A-13B are alternative perspective view and a cross-sectional view of the cap 5 and the piston 100.

Figure 14A:
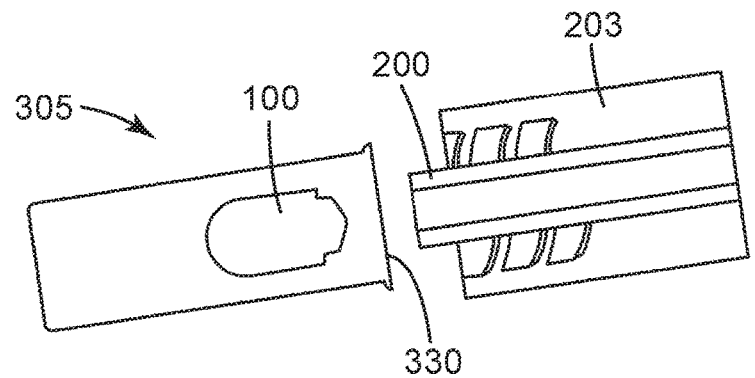
FIGS. 14A-14B are cross sectional views of a male medical implement cap receiving a male protrusion and a sleeve of a male medical implement.
Figure 14B:
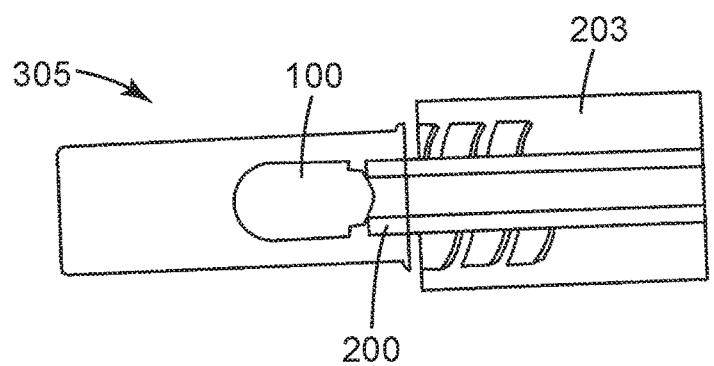
Figure 15:
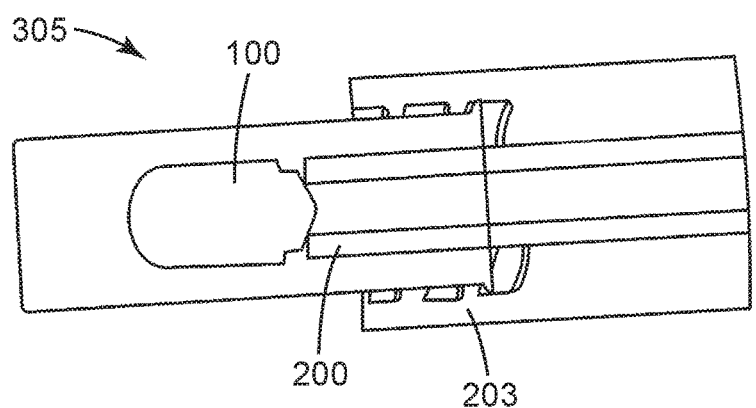
FIG. 15 shows the cap fully engaged on a male protrusion of a medical implement.

FIGS. 14A-14B are cross sectional views of a male medical implement cap 305 receiving a male protrusion 200 and a threaded sleeve 203 of a male medical implement. The male protrusion 200 typically extends beyond the sleeve 203, and therefore is inserted or is received first into the cap 305. In a preferred implementation, the piston 100 is placed in the cap 305 at a depth or distance from the opening 330 to the cap 305, so as to be contacted for moving by the male protrusion 200 before the threads at the opening 330 of the cap 305 come into contact with the threaded sleeve 203. FIG. 15 shows the cap 305 fully engaged on a male protrusion 200 of a medical implement. When the tapered male protrusion 200 wedges into the diameter of the opening of the cap 305, the recesses will have filled with the cleaning solution or fluid, and the friction-based fitting will maintain the cleanliness of the male protrusion 200. Some of the cleaning solution or fluid will also exit the cap from the vents, to fill at least a portion of the sleeve 203 surrounding the male protrusion 200, and clean all or some of the threads of the sleeve 203.

Figure 16A:
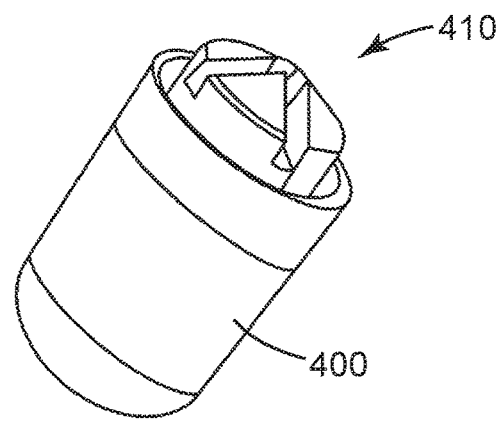
FIGS. 16A-16C show various implementations of a male protrusion interface surface of the piston.
Figure 16B:
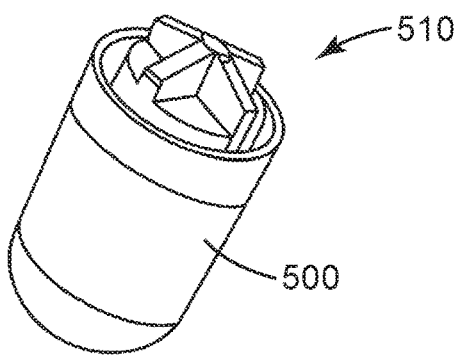
Figure 16C:
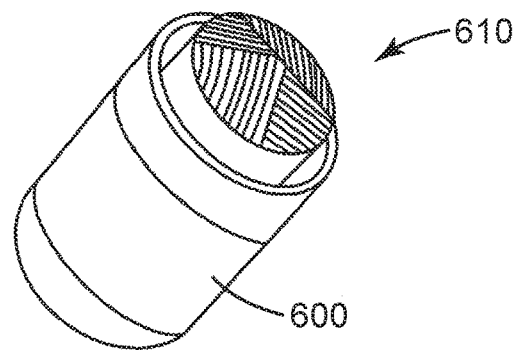

FIGS. 16A-16C show various implementations of a male protrusion interface surface 410, 510, 610 of the piston 400, 500, 600. The rear surface or male protrusion interface may include any number of raised ridges, or conversely, cut-in ridges, to inhibit a seal of the lumen of the male protrusion, and to allow a flow of the cleaning solution or fluid through the ridges as desired. These grooves or ridges may inhibit sealing, which can contribute to an undesired pressure buildup in the lumen, or even an out-gas from the lumen to further move the piston or the cleaning solution or fluid in unwanted ways. Accordingly, the ridges on the piston are configured for specific connection with the male protrusion while inhibiting the sealing of the lumen.

Figure 17:
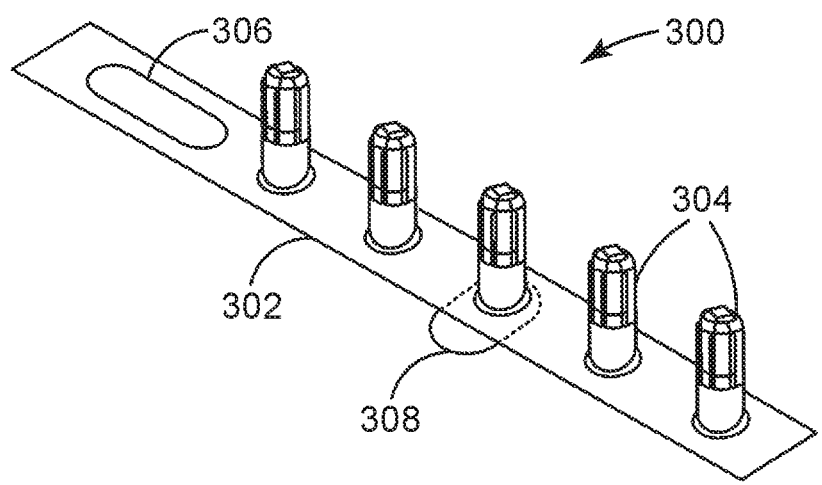
FIG. 17 illustrates a cleaning system having five caps connected to a strip of material.

FIG. 17 illustrates a cleaning system 300, in which a number of caps 304, as substantially described above, are connected with a strip 302 or other shape of planar material. In some implementations, the opening of the caps 304 are formed with a flattened ridge or periphery, and each cap 304 is attached to the strip 302. The strip 302 can be a foil strip, or can be a harder, more rigid piece of material. In use, a practitioner simply pulls or peels away each cap 304 from the strip 302 individually, to expose the opening to the inner cavity, and allow the cap 304 to be placed over a male protrusion of the male luer. In still other implementations, the strip 302 can be formed with holes, and each cap 304, individually or by group, can be placed through the holes until a seal or tab 308, already provided over the opening of the cap 304, is connected with the strip 302. The strip 306 can include an aperture or hole 306 to allow the cleaning system 300 to be attached to another object, such as an intravenous (IV) pole or the like.

The cap and the piston can be made from polyethylene or another material that is stable when in the presence of alcohol or other cleaning agent. The cleaning agent can be any chemical, substance or material that cleans the site of bacterial or even viral microorganisms, or any carrier that contains such chemical, substance or material. Examples of a cleaning agent include isopropyl alcohol, chlorhexidine, povidone-iodine, hydrogen peroxide, soap, and hydrochloric acid.

Although a few embodiments have been described in detail above, other modifications are possible. Other embodiments may be within the scope of the following claims.

The invention claimed is:

1. A cleaning device for a medical implement having a male protrusion, the cleaning device comprising:
    a housing defining an inner cavity, the housing having an inner wall that encloses the inner cavity and an opening, the inner wall having a recess near the opening to the housing;
    a cleaning solution in the inner cavity of the housing; and
    a movable piston within the inner cavity having a rearward end facing the opening of the housing and a forward end opposite the rearward end, the rearward end surrounded by a flexible skirt that flares outward to abut the inner wall near the recess to maintain the cleaning solution in the inner cavity prior to receipt of the male protrusion into the inner cavity, the rearward end of the movable piston configured to contact a distal end of the male protrusion to move the piston toward a distal end of the housing opposite the opening of the housing to provide a portion of the cleaning solution to the male protrusion,
    wherein the diameter of the inner wall is wider at the recess than at the distal end of the housing and at the opening, and
    wherein the flexible skirt flares away from the piston in a direction that is opposite from the forward end and is sized to be slightly wider than the recess and the inner wall of the inner cavity of the housing.

2. The cleaning device in accordance with claim 1, further comprising a removable seal coupled to the opening of the housing to seal the opening and maintain the piston and the cleaning solution within the inner cavity prior to receipt of the male protrusion.

3. The cleaning device in accordance with claim 1, wherein the housing further includes one or more threads extending out from an outer surface of the housing proximate the opening.

4. The cleaning device in accordance with claim 1, wherein the housing further includes one or more ridges extending out from an outer surface of the housing near the distal end of the housing opposite the opening.

5. The cleaning device in accordance with claim 1, further comprising venting means between the opening and the recess.

6. The cleaning device in accordance with claim 1, wherein the inner cavity is cylindrical.

7. The cleaning device in accordance with claim 6, wherein the recess extends around the circumference of the inner cavity.

8. The cleaning device in accordance with claim 6, wherein the recess occupies less than the full circumference of the inner cavity.

9. The cleaning device in accordance with claim 1, wherein the rearward end of the movable piston has a male protrusion interface comprising one or more features selected from the group consisting of grooves, channels and raised portions.

10. The cleaning device in accordance with claim 9, wherein the raised portions of the male protrusion interface of the piston comprise raised ridges, wherein the male protrusion of the medical implement defines a lumen, and wherein the raised portions of the male protrusion interface contact the male protrusion while inhibiting sealing the lumen.

11. The cleaning device in accordance with claim 1, wherein the housing is a cap.

* * * * *

UNITED STATES PATENT AND TRADEMARK OFFICE
CERTIFICATE OF CORRECTION

PATENT NO. : 9,999,471 B2  
APPLICATION NO. : 13/910053  
DATED : June 19, 2018  
INVENTOR(S) : Bobby E. Rogers Page 1 of 1

It is certified that error appears in the above-identified patent and that said Letters Patent is hereby corrected as shown below:

On the Title Page

<u>Column 2 (Abstract)</u>  
Line 3  After "cavity" delete "by".  
Line 11  After "contact" delete "couple with".

Signed and Sealed this
Twenty-first Day of August, 2018

Andrei Iancu
*Director of the United States Patent and Trademark Office*